United States Patent [19]

Sjönell

[11] Patent Number: 5,042,496
[45] Date of Patent: Aug. 27, 1991

[54] METHOD FOR MEASURING BLOOD PRESSURE AND A BLOOD-PRESSURE MEASURING DEVICE FOR CARRYING OUT THE METHOD

[76] Inventor: Göran Sjönell, Askrikevägen 11, 181 46 Lidingö, Sweden

[21] Appl. No.: 523,873

[22] Filed: May 16, 1990

[30] Foreign Application Priority Data

May 23, 1989 [SE] Sweden ............................. 8901831

[51] Int. Cl.$^5$ ............................................. A61B 5/02
[52] U.S. Cl. .................................................. 128/677
[58] Field of Search ................. 128/672, 676, 677–679

[56] References Cited

U.S. PATENT DOCUMENTS 3,926,179 12/1975 Petzke et al.
4,768,518 9/1988 Peltonen ............................. 128/677
4,869,261 9/1989 Penáz ................................. 128/677

FOREIGN PATENT DOCUMENTS 880338 5/1988 PCT Int'l Appl.
8805283 7/1988 PCT Int'l Appl.

OTHER PUBLICATIONS

Article: Sphygmomanometer Cuff and the Accuracy of Indirect Measurement of Blood Pressure, M. J. Karvonen et al, 5/1964, American Journal of Cardiology (pp. 688–693).
Article: Noninvasive Automatic Determination of Mean Arterial Pressure, M. Ramsey III, 1/1979, 2200 Medical & Biological Engineering & Computing (pp. 11–18).
Article: Criteria in the Choice of an Occluding Cuff for the Indirect Measurement of Blood Pressure, 1/1977, Medical & Biological Engineering & Computing (pp. 2–10).

Primary Examiner—Lee S. Cohen
Assistant Examiner—Krista M. Pfaffle
Attorney, Agent, or Firm—Burns, Doane, Swecker & Mathis

[57] ABSTRACT

A blood pressure measuring device includes a cuff (1) intended to be placed around the upper arm or the thigh of a person, a pressure sensor (2) and a manometer (3). The values measured by the cuff are automatically corrected in a correction unit (4), so as to eliminate systematic errors contingent on the pulse frequency and the pressure level prevailing at the moment of measuring blood pressure. The device also includes an infeed unit (6) into which data relating to the person's age, sex and arm circumference is inserted. The correction unit (4) then uses this data to correct the values measured by the cuff, so that systematic errors contingent on age, sex and arm circumference will be eliminated. The corrective values of the systolic and diastolic pressure are then displayed on a display unit (8), these pressure values being independent of the person's age, sex, arm circumference, pulse frequency and pressure level.

2 Claims, 1 Drawing Sheet

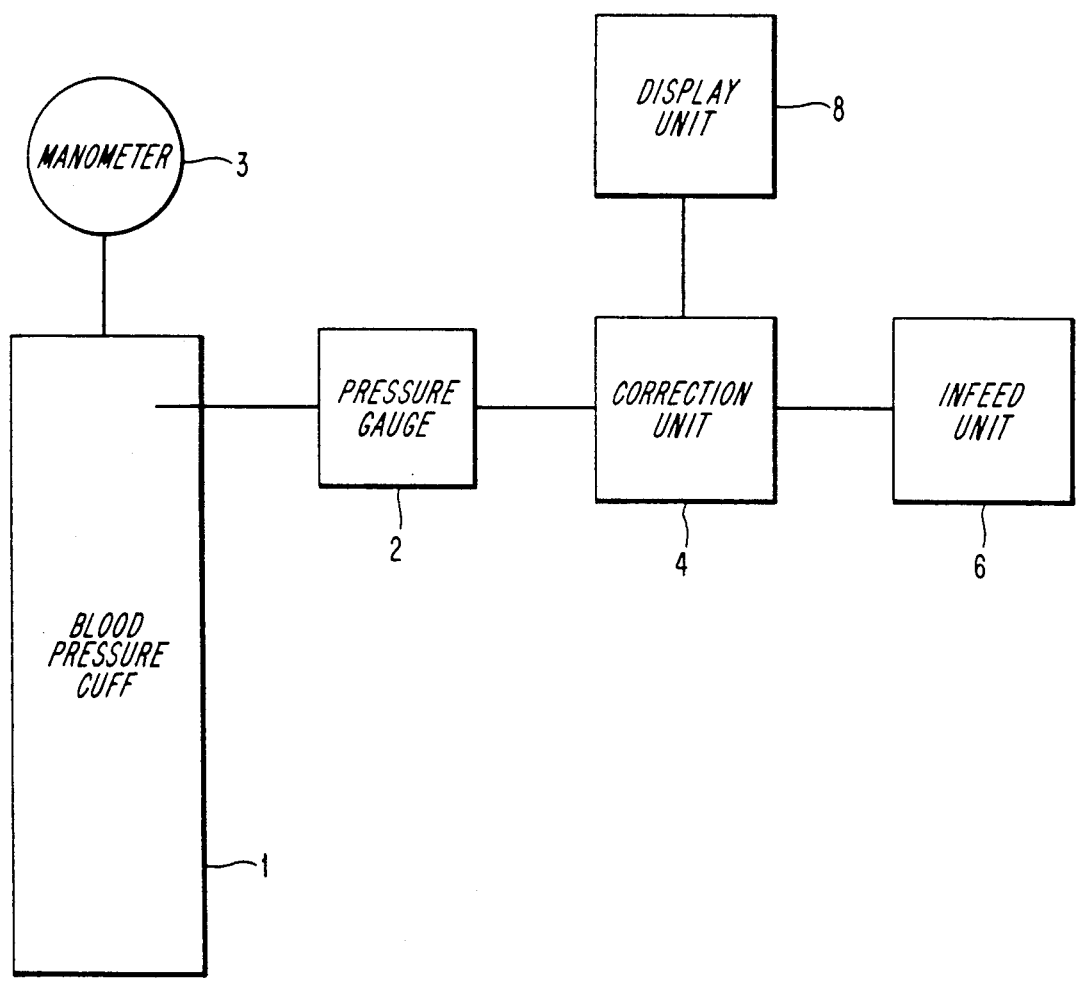

METHOD FOR MEASURING BLOOD PRESSURE AND A BLOOD-PRESSURE MEASURING DEVICE FOR CARRYING OUT THE METHOD

BACKGROUND OF THE INVENTION

The present invention relates to a method for measuring blood pressure, and to a blood-pressure measuring device for carrying out the method.

Blood pressure is normally measured with the aid of a blood-pressure cuff or sleeve which is applied around the upper arm of the patient (or sometimes around the patient's thigh).

The prevailing method of measuring blood pressure involves the use of a universal cuff, which is used for all patients. Research within this field, however, has shown that serious measurement errors can occur when measuring with the aid of an universal cuff, since systematic errors are added to the true blood pressure value.

Due to the presence of soft tissue between the blood vessel and the bone in the centre of the arm (or the thigh) around which the cuff is placed, the use of one and the same cuff with arms of mutually different sizes or thicknesses does not give a clear reading of the true blood pressure. In the case of a thin arm, the pressure read-off will be relatively low, whereas in the case of a thick arm, the pressure read-off will be relatively high, even if that in reality the persons concerned have mutually the same blood pressure.

U.S. Pat. No. 3,812,844 teaches a blood pressure cuff incorporating automatic compensation of the measured values in dependence on variations in the diameter of the measurement object. This is effected by dividing the blood pressure cuff into a plurality of longitudinally extending sections, each of which is associated with a respective indicating range on the measuring device. This requires the use of a special blood pressure cuff in order to obtain a corrected measurement value, this value only being corrected with respect to the circumference of arms and not with respect to the remaining parameters aforementioned.

It is also found that the pulse frequency of a patient at the time of measuring blood pressure will also influence the blood pressure value measured with the universal cuff. At high pulse frequencies, the universal cuff tends to indicate an excessively high pressure value. This may depend, for instance, on the extent to which the heart is filled prior to blood being pumped therefrom. At high pulse rates, the heart is not completely filled, and consequently the heart beats will not be as powerful as heart beats at low pulse frequencies.

When measuring the blood pressure of elderly people with the aid of an universal cuff in a conventional manner, the true blood pressure value is exaggerated or overestimated, i.e. the pressure value read-off is somewhat higher than the true blood pressure value. This is probably due to the fact that the veins and arteries become stiffer with age.

It is also found that when measuring blood pressure with an universal cuff, the blood pressure of women is exaggerated overestimated in comparison with blood pressure of men, i.e. if a man and a woman have equal blood pressures in reality, the blood pressure reading in the case of the woman will be higher than that for the man.

The pressure level of the patient at the time of measuring blood pressure will also influence the blood pressure value measured by the universal cuff, wherein a low blood pressure results in depreciation of the true blood pressure, whereas a high pressure level results in exaggeration of the true blood pressure.

The systematic errors contingent on variations in the aforesaid parameters: age, sex, arm circumference, pulse frequency and pressure level, cause the blood-pressure values obtained with the universal cuff to incorporate in reality errors in the order of 5-10 mm Hg with respect to both the systolic and diastolic pressure.

The limit for treatment of a patient for, e.g., hypertony, i.e. increased blood pressure, may depend on whether the patient has a lower pressure, i.e. a diastolic pressure, of 95 or 100. Thus, the systematic errors occurring when using the universal cuff are decisive in many instances in deciding whether a patient is sick or well and whether the patient requires treatment or not.

The present invention attempts to solve the aforesaid problems, by introducing corrections for the aforesaid systematic errors occurring when measuring blood pressure with an universal or unitary cuff, thereby to eliminate the error margin to the greatest possible extent.

THE DRAWING

The inventive blood-pressure measuring device will now be described in more detail with reference to the accompanying drawing, which illustrates schematically one embodiment of said blood pressure measuring device.

DESCRIPTION OF A PREFERRED EMBODIMENT OF THE INVENTION

The single Figure of the drawing illustrates a blood pressure cuff, by which is understood a conventional cuff with regard to its basic construction of casing, lining, and burr-fastener or VelcroR fastener. The cuff 1 is provided with a manometer 3, in a conventional manner. The cuff 1 is also connected to a pressure gauge 2 which sends a pressure value dependent on the pressure in the cuff 1 to a correction unit 4, which functions to correct the systematic errors contingent on variations in parameters characteristic of the patient concerned, i.e. age, sex, arm circumference, pulse frequency and pressure level occasion at which blood-pressure is measured. The correction unit 4 is also connected to an infeed unit 6 and a display unit 8.

A device for measuring blood pressure in the home and without the assistance of a doctor can, for instance, be constructed in the above manner. Thus, when the cuff 1 is applied, for instance, to the upper arm, the pressure sensor 2 will send to the correction unit 4 a pressure-level value obtained from the cuff 1. Also sent to the correction unit 4 is a pulse-frequency value obtained with the aid of a known oscillometric technique (not shown). The correction unit 4 will automatically correct the pressure value sensed by the cuff in respect of those systematic errors dependent that are contingent on pulse frequency and pressure level at the moment of measuring blood pressure. This can be effected with the aid of regression coefficients. The patient concerned then feeds in data concerning his/her age, sex and arm circumference manually with the aid of infeed unit 6, which converts this information into signals, which are then transmitted to the correction unit 4. The correction unit 4 then functions to correct the blood pressure sensed by the cuff in respect of those systematic errors which are contingent on the patient's age, sex and arm circumference. The arm circumference can be readily measured, with the aid of a "tape measure" mounted on the cuff, so as to enable the arm circumference to be read-off when the cuff is placed around the upper arm in a conventional manner. The correction unit 4 then sends the corrected values to the display unit 8, where the true pressure values for the systolic and diastolic pressures are displayed in a respective display window. The pulse frequency can also be displayed on a further display window provided on the display unit 8. Thus, the pressure values obtained are independent of the person's age, sex, arm circumference and pulse frequency and pressure level at the time of measuring blood pressure.

The present invention was tested by measuring the diastolic pressure of 50 people with the aid of the universal cuff (12 cm wide), with direct pressure measurement and with the inventive blood pressure measuring device. The average value of the pressure values measured with the universal cuff was 84.3 mm Hg. With direct pressure measurement (which is highly reliable) the average value was 76.6 mm Hg. When using the inventive blood-pressure measuring device, a mean value of 76.52 mm Hg was obtained. Thus, it is possible to obtain precise pressure values when using the inventive blood-pressure measuring device, without using direct pressure measurement, which is often impractical from the aspect of cost and not entirely free from complications. Measuring of blood pressure should be a simple operation, since it constitutes a routine examination carried out at frequent intervals. Furthermore, measuring of blood pressure should be as exact as possible. This is achieved with the inventive blood-pressure measuring device. The aforesaid trial also showed that individual deviations with respect to the aforesaid variables age, sex, arm circumference, pulse frequency and pressure level measured with the inventive blood-pressure measuring device in comparison with conventional blood-pressure measuring devices (using the universal cuff) were found to be in the region of 2–17 mm Hg.

Although the invention has been described essentially with respect to measuring blood pressure on the upper arm, it will be understood that the invention can also be applied for measuring blood pressure on the thigh.

The embodiment illustrated in FIG. 1 merely comprises an example of how the invention can be realized and is not limitive of the invention, the scope of which is defined in the following claims.

I claim:

1. A method for measuring blood pressure by the use of a blood pressure cuff and a pressure gauge connected to said cuff, said method including the steps of:

placing said cuff around a limb of a patient to obtain a pressure-level value from said pressure gauge, determining a pulse frequency value of the patient's pulse, providing a connection unit connected to said pressure gauge, said correction unit being operable to make corrections in said pressure level for blood-pressure measuring errors occurring as a function of pulse frequency, pressure level, patient sex, patient age, and limb circumference, supplying said pressure level value and said pulse frequency value to said correction unit, and causing said correction unit to make corrections for said errors occurring as a function of said pulse frequency value and said pressure level value, providing an infeed unit connected to said correction unit, said infeed unit being operable to supply to said correction unit data corresponding to patient sex, patient age, and limb circumference, actuating said infeed unit to supply said data to said correction unit, and causing said correction unit to make corrections for errors occurring as a function of the patient sex, patient age, and limb circumference, and providing a display unit connected to said correction unit, and causing said display unit to display a blood-pressure level value corrected for errors occurring as a function of pulse frequency value, pressure level value, patient sex, patient age, and limb circumference.

2. A blood pressure measuring device comprising:

a cuff adapted to be placed around a limb of a patient, a pressure gauge connected to said cuff for providing a pressure level value, a correction unit for making corrections in said pressure level value for blood-pressure measuring errors occurring as a function of pulse frequency value, pressure level value, patient sex, patient age, and limb circumference, said correction unit connected to said pressure gauge for receiving therefrom said pressure level value and being adapted to receive a pulse frequency value relating to the patient's pulse, an infeed unit connected to said correction unit for supplying thereto data corresponding to patient sex, patient age, and limb circumference, and a display unit connected to said correction unit for receiving therefrom and displaying a blood-pressure level value corrected for errors occurring as a function of pulse frequency value, pressure level value, patient sex, patient age, and limb circumference.

* * * * *